United States Patent [19]
Verwey et al.

[11] 3,962,277
[45] June 8, 1976

[54] ACETIDINE DERIVATIVES

[75] Inventors: Jan Verwey, Leiden; Hong Sheng Tan, Bleiswijk, both of Netherlands

[73] Assignee: Gist-Brocades N.V., Delft, Netherlands

[22] Filed: Oct. 6, 1975

[21] Appl. No.: 619,843

Related U.S. Application Data

[62] Division of Ser. No. 440,725, Feb. 8, 1974.

[30] Foreign Application Priority Data
Feb. 9, 1973 United Kingdom............... 6576/73

[52] U.S. Cl........................... 260/326 S; 260/239.1; 260/243 C; 260/251 QA; 260/281 GP; 260/309.5
[51] Int. Cl.²................................. C07D 209/34
[58] Field of Search................ 260/326 S

[56] References Cited
UNITED STATES PATENTS
3,840,556  10/1974  Kukolsa................ 260/326.37

*Primary Examiner*—Gerald A. Schwartz
*Attorney, Agent, or Firm*—Hammond & Littell

[57] ABSTRACT
A new azetidine derivative of the formula:

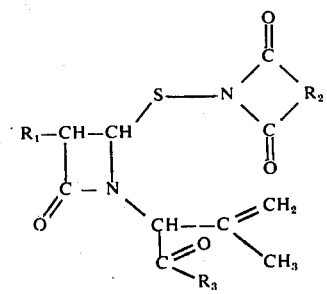

wherein $R_1$ represents a penicillin- or cephalosporin-amido group, $R_2$ represents one of the groups of the following formulae:

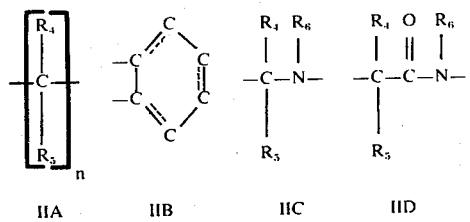

IIA     IIB     IIC     IID wherein $R_4$, $R_5$ and $R_6$ are the same or different and each represents a hydrogen atom or a lower alkyl or alkenyl group, $n$ represents 2 or 3 and - in case formula IIB represents a phenyl group - this group may carry one to four further substituents selected from the group consisting of halogen atoms and lower alkyl, lower alkenyl and phenyl groups, $R_3$ represents an amino group of the formula

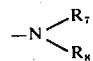

wherein $R_7$ represents a hydrogen atom or a lower alkyl group and $R_8$ represents a lower alkyl group, or $R_3$ represents a N,N'-disubstituted hydrazino group wherein the substituents are lower alkyl groups, e.g. the N,N'-diisopropylhydrazino group, or $R_3$ represents the group —$OR_9$, wherein $R_9$ represents a hydrogen atom, a lower alkyl group, which group may be substituted by 1 to 3 halogen atoms or by 1 or 2 phenyl groups, werein the phenyl groups may be substituted by a methoxy or a nitro group, or $R_9$ represents a phenacyl group or a salt-forming cation, and corresponding azetidine derivatives of formula I wherein the double bond in the propenyl side chain has been shifted from the 2- to the 1-position, which are versatile intermediates in the process of preparing cephalosporanic and penicillanic derivative.

23 Claims, No Drawings

ACETIDINE DERIVATIVES

This is a division of Ser. No. 440,725, filed Feb. 8, 1974.

This invention relates to new azetidine derivatives, to a process for their preparation, and to a new process for the preparation of cephalosporanic acid derivatives using the azetidine derivatives as starting materials.

It is an object of the present invention to provide hitherto unknown azetidine derivatives conforming to the general formula:

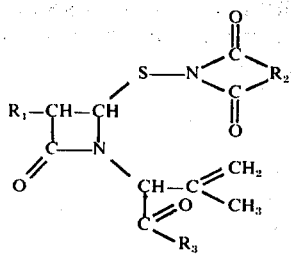

I wherein $R_1$ represents a penicillin- or cephalosporinamido group, $R_2$ represents one of the groups of the following formulae:

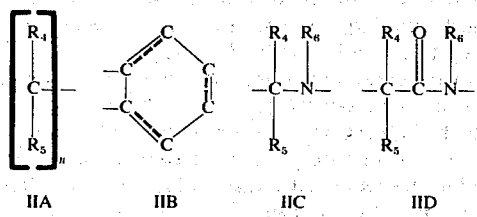

IIA   IIB   IIC   IID wherein $R_4$, $R_5$ and $R_6$ are the same or different and each represents a hydrogen atom or a lower alkyl or alkenyl group, n represents 2 or 3 and - in case formula IIB represents a phenyl group - this group may carry one to four further substituents selected from the group consisting of halogen atoms and lower alkyl, lower alkenyl and phenyl groups, $R_3$ represents an amino group of the formula

wherein $R_7$ represents a hydrogen atom or a lower alkyl group and $R_8$ represents a lower alkyl group, or $R_3$ represents a N,N'-disubstituted hydrazino group wherein the substituents are lower alkyl groups, e.g. the N,N'-diisopropylhydrazino group, or $R_3$ represents the group $-OR_9$, wherein $R_9$ represents a hydrogen atom, a lower alkyl group, which group may be substituted by 1 to 3 halogen atoms or by 1 or 2 phenyl groups, wherein the phenyl groups may be substituted by a methoxy or a nitro group, or $R_9$ represents a phenacyl group or a salt-forming cation, and corresponding azetidine derivatives of formula I wherein the double bond in the propenyl side chain has been shifted from the 2- to the 1-position.

For the purposes of this application the latter azetidine derivatives will be indicated by the term "iso-azetidine derivatives".

By the expression "penicillin- or cephalosporinamido group" is meant a 6β-acylamido group, which is known to those skilled in the art, in both natural and synthetic penicillins and cephalosporins.

By the terms "lower alkyl" and "lower alkenyl" as employed herein, alone or in conjunction with other designated groups, is meant straight- or branched-chain alkyl and alkenyl groups containing from one to four carbon atoms, e.g. methyl, ethyl, allyl, isopropyl, butyl, and t-butyl. Similarly, the term "lower alkoxy" as used herein, alone or in conjunction with other designated groups, means straight-chain or branched-chain alkoxy groups containing from one to four carbon atoms. The halogens referred to may be chlorine, bromine, iodine or fluorine.

By the term "salt-forming cation" as used for symbol $R_9$ is meant alkali metal and alkaline earth metal ions, for example sodium, potassium and calcium ions.

Preferably, the symbols $R_4$, $R_5$ and $R_6$ in the formulae IIA to IID represent a hydrogen atom or a methyl or ethyl group. Suitable groups represented by the formula:

$$-N\overset{\overset{O}{\|}}{\underset{\underset{O}{\|}}{C}}\overset{}{\underset{C}{\diagdown}}R_2$$

are, for example: succinimido, phthalimido, hexahydrophthalimido, 1,5,5-trimethylhydantoin-3-yl, 3,3-dimethylglutarimido, 3-ethyl-3-methylglutarimido and 5-ethyl-1-methyl-5-phenyl-2,4,6-trioxohexahydropyrimidin-3-yl. $R_3$ preferably represents the group $-OR_9$, wherein $R_9$ represents a hydrogen atom, a methyl or benzyl group or a sodium or potassium ion.

According to a feature of the present invention the azetidine derivatives of general formula I are prepared by the process which comprises reacting a penicillanic sulphoxide derivative of the general formulae:

IIIA   IIIB wherein $R_1$ is as hereinbefore defined, and $R_3'$ has the same significance as defined above for symbol $R_3$, except that when $R_3'$ represents a group $-OR_9$, $R_9$ does not represent a salt-forming cation, but $R_9$ moreover represents a silyl group of one of the following formulae:

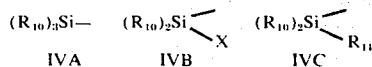

wherein the symbols $R_{10}$ are the same or different and each represents a lower alkyl or alkoxy group (optionally substituted by halogen atoms), or a phenyl group, X represents a halogen (preferably chlorine) atom and $R_{11}$ represents a penicillanic sulphoxide acyl group of the general formulae:

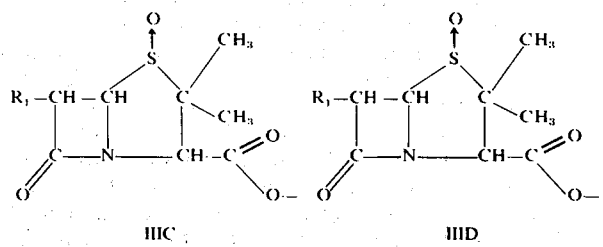

wherein $R_1$ is as hereinbefore defined, with a silicon-containing compound of the general formula:

wherein $R_2$ and $R_{10}$ are as hereinbefore defined, under anhydrous conditions, in an inert organic solvent at temperatures between 50° and 180°C.

As is apparent from the formulae III the oxygen atom of the sulphoxide grouping may be in β- or α-position in relation to the penicillin nucleus; in this application these isomers are referred to as S- and R-sulphoxides, respectively.

Preferably, the symbol $R_3'$ in the starting materials of formulae IIIA and B a group —$OR_9$, wherein $R_9$ represents a hydrogen atom, a methyl or benzyl group, or a silyl group as defined herein above. Suitable silyl groups are for example: triethoxysilyl, tributoxysilyl, dimethoxy methylsilyl, diethoxy methylsilyl, dimethyl methoxysilyl, dimethyl ethoxysilyl, butoxy dimethylsilyl, tri(2-chloroethoxy)silyl, tri(2-chloropropoxy)silyl, trimethyl silyl, diphenyl methylsilyl, etc.

The reaction is advantageously carried out at a temperature between 70° and 120°C, depending on the reflux temperature of the solvent employed. Reaction times of 15 minutes to one day appeared to be necessary for good conversion yields (e.g. of up to 70% of the theoretical yield) in the indicated temperature range.

Examples of silicon-containing compounds of formula V which may be utilized in the aforesaid process are succinimides, phthalimides, hexahydrophthalimides, hydantoins, glutarimides and barbiturates, substituted on the nitrogen atom by the group($R_{10}$)$_3$ Si— wherein $R_{10}$ is as hereinbefore defined and is preferably a methyl group. Specific examples of such reactants are N-trimethylsilylsuccinimide, 3-trimethylsilyl-1,5,5-trimethylhydantoin, N-trimethylsilylphthalimide, N-trimethylsilylhexahydrophthalimide, N-trimethylsilyl-3,3-dimethylglutarimide, N-trimethylsilyl-3-ethyl-3-methylglutarimide and 3-trimethylsilyl-5-ethyl-1-methyl-5-phenyl-2,4,6-trioxohexahydropyrimidine(3-trimethylsilyl-5-ethyl-1-methyl-5-phenyl-malonylurea).

The molar amount of the silicon-containing compound according to formula V which has to be employed depends on the significance of symbol $R_3'$ in formulae IIIA or B. When the said symbol represents a hydroxy group, sufficient silicon-containing compound must be used as to silylate the carboxy group of the penicillanic sulphoxide before the sulphur-containing ring is opened. When $R_3'$ represents a hydroxy group, at least 3 moles of the silicon reactant of formula V are employed per mole of penicillanic sulphoxide. Advantageously still larger molar amounts of the silicon reactant (up to 50 moles per mole of sulphoxide) are used. The silicon-containing compound may then even act as the solvent wherein the reaction is carried out.

Usually however, an additional solvent is added to the reaction mixture. The inert organic solvents employed in the process are those which cannot influence the reaction, i.e. preferably consisting of molecules which are not silylated under the reaction conditions employed. Advantageously aprotic polar solvents are used.

Examples of suitable solvents are: hexamethylphosphotriamide, dimethoxyethane, N,N-diethylmethylsulphonamide and methylisobutyl ketone. Preferred solvents are: benzene, toluene, acetonitrile, benzonitrile, nitrobenzene, N,N,N',N'-tetramethylurea, N-acetylsuccinimide, N-acetylphthalimide, 3-acetyl-1,5,5-trimethylhydantoin, dimethylacetamide and dimethylformamide. Particularly, preferred are the latter six solvents or mixtures of these. Sometimes the yield of the process can be improved by adding acetic acid or trimethylsilyl acetate to the reaction mixture.

When starting materials of formulae III A or B are used in the free acid form, i.e. when $R_3'$ represents a hydroxy group, the penicillanic sulphoxide acid will first be silylated by reaction with the silicon-containing compounds of formula V, whereupon these silylated penicillanic sulphoxide derivatives will be converted with further amounts of the silicon-containing compounds of formula V into azetidine derivatives of general formula I, wherein the acid group is silylated too.

During the further isolation and/or purification processes the silyl group is removed again form the azetidine compound, thus resulting in an azetidine derivative of general formula I in the free acid form or a salt thereof, i.e. wherein $R_3$ represents a hydroxy group or $R_3$ is a group —$OR_9$, wherein $R_9$ represents a salt-forming cation as defined hereinbefore.

Whether the azetidine derivative of formula I is obtained in the form of a free acid or a salt thereof depends on the isolation and purification procedures employed.

It will be appreciated that when starting materials of formulae III A or B, wherein $R_3'$ is a group —$OR_9$ and $R_9$ represents a silyl group of formulae IV A to C, are used, the process will proceed in the same way and will also result in azetidine derivatives of formula I in the free acid form or a salt thereof, obtained via corresponding intermediate silylated azetidine derivatives. On the other hand, when $R_3'$ in the starting penicillanic sulphoxide derivatives of formulae III A or B represents an amino group

wherein $R_7$ and $R_8$ are as hereinbefore defined, or represents a N,N'-disubstituted hydrazino group as defined hereinabove, or a group —$OR_9$, wherein $R_9$ is as hereinbefore defined in relation to formula III, but does not represent a hydrogen atom or a silyl group of formulae IV A to C, the reaction with a silicon-containing compound of formula V will not affect the group $R_3'$ and accordingly, the group $R_3$ in the azetidine derivative of general formula I thus obtained is identical to the group $R_3'$ of the penicillanic sulphoxide starting material.

Azetidine derivatives of formula I, wherein $R_3$ is a group —$OR_9$, wherein $R_9$ represents a (eventually substituted) lower alkyl group, as defined hereinabove in relation to formula I, may also be prepared by converting an azetidine derivative of formula I, wherein $R_3$ represents a hydroxy group, obtained according to one of the processes described hereinabove, into a corresponding ester.

For example, azetidine methyl esters of formula I can be prepared by reacting a corresponding azetidine derivative of formula I in the free acid form with diazomethane in an inert organic solvent, such as diethyl ether. The azetidine free acid compound can be used in this reaction as such or dissolved or suspended in an appropriate organic medium, such as tetrahydrofuran.

The azetidine derivatives obtained according to one of the processes described hereinabove usually have the structure indicated in formula I, i.e. with a (substituted) prop-2-enyl side chain in the molecule. Sometimes the corresponding prop-1-enyl (conventionally indicated by propenyl)-isomers may be obtained, however. In some cases the reaction between a penicillanic sulphoxide derivative of formula III and a silicon-containing compound of formula V results directly in a so-called iso-azetidine (i.e. propenyl) derivative; in other cases a mixture of propenyl- and prop-2-enyl-isomers is obtained, from which each of the isomers can be isolated by chromatography on silica gel.

A prop-2-enyl azetidine derivative of formula I may also be converted into a corresponding propenyl isomer, for example by gentle heating of the prop-2-enyl compound (preferably in the form of an ester) with triethylamine in a suitable organic medium, such as tetrahydrofuran.

The azetidine derivatives obtained according to the processes described hereinabove may be separated from the reaction mixture by application of known procedures, for example:

a. the reaction mixture is evaporated to dryness and an organic solvent is added to the residue; the azetidine derivative is then obtained by fractional precipitation and/or crystallization, or b. the reaction mixture is evaporated to dryness and the azetidine derivative is obtained fom the residue by chromatography on silica gel.

When the reaction mixture contains an azetidine derivative in the free acid form this may be isolated as such from the reaction mixture or it may first be converted into a salt thereof.

In order to prepare potassium salts, for example, the reaction mixture is first concentrated and filtered; to the filtrate is then added for example potassium-2-ethylcaproate (if desired dissolved in a suitable solvent, such as propanol) or potassium acetate (which is usually added as such in the form of a powder), whereupon the precipitated potassium salt of the azetidine derivative is separated from the reaction mixture.

The penicillanic sulphoxides of formulae III A or B, employed as starting materials in the process described above, can be obtained by treatment of the corresponding penicillanic acids of the following formula:

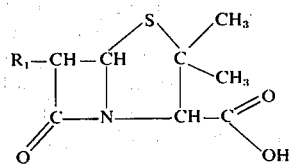

wherein $R_1$ is as defined hereinabove,
with an oxidizing agent. For example, for this purpose the penicillanic acid derivative is treated in an inert organic solvent or water with a substance affording active oxygen, such as sodium periodate, a per-acid, hydrogen peroxide, iodobenzene dichloride, or with ozone. The penicillanic sulphoxide derivatives of formulae III A or B, wherein $R_3'$ is other than a hydroxy group, can be prepared from a corresponding penicillanic free acid, either before or after its conversion into a sulphoxide.

As already described above a penicillanic sulphoxide of formula III in the free acid form can be silylated during the process of the invention by reaction with the silicon-containing compound of formula V.

But a penicillanic sulphoxide of formula III, wherein $R_3'$ represents a hydroxy group, can also be converted into a corresponding derivative with a silylated carboxy group in a separate reaction step before the process of the invention is carried out, by reacting the free acid with a silylating agent, such as, for example, N,O-bis(-trimethylsilyl)acetamide, in an inert organic solvent.

It will be appreciated that when silylating agents wherein two halogen atoms are attached directly to the silicon atom (such as, for example, dichloromethylsilane), are employed in this process, two molecules of the penicillanic acid derivative may react with one molecule of the silylating agent, resulting in a silyl compound, wherein two penicillanic sulphoxide acyl groups of formulae IIIC or D are attached to the silicon atom (cf. formula IV C). Depending on the reactants and/or reaction conditions employed it is also possible that only one molecule of the penicillanic acid derivative reacts with one molecule of the dihalo-silylating agent, resulting in a silylated penicillanic sulphoxide derivative wherein one halogen atom is still attached to the silicon atom (cf. formula IV B).

All these types of silylated penicillanic sulphoxide derivatives may be used as such in the process of the invention.

The 6β-acylamido group $R_1$ in the penicillanic acids of formula VI, which are employed as starting materials in the process of preparing the penicillanic sulphoxides of formula III, can be any group, which is known to those skilled in the art, in the field of both natural and synthetic penicillins and cephalosporins. The group of suitable 6β-acylamido side chains $R_1$ include, for example, those of the following general formula:

   VII wherein $Q_1$ represents a hydrogen atom or a group linked to the nitrogen atom by a carbon or sulphur atom, and $Q_2$ represents a hydrogen atom or a lower alkyl, hydroxy, amino or phenyl(lower) alkyl group, or $Q_1$ and $Q_2$ together with the nitrogen atom to which they are attached collectively represent a heterocyclic group, e.g. an optionally substituted succinimido, phthalimido, oxazolidinyl or imidazolidinyl group, or $Q_1$ and $Q_2$ together form an aralkylidene or alkylidene group, e.g. benzylidene, isopropylidene or salicylidene.

Preferably, $Q_2$ represents a hydrogen atom and $Q_1$ is a group of one of the following formulae:

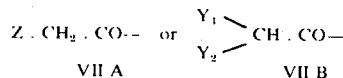

VII A          VII B wherein Z represents:
a. an aliphatic hydrocarbon group having at most 6 carbon atoms and which can have a double bond.
b. a phenyl or phenoxy group, which groups may be substituted by halogen atoms, or hydroxy, lower alkyl, lower alkoxy, nitro or amino groups,
c. a(lower alkyl)thio group,
d. a 3-amino-3-carboxy-propyl group
and $Y_2$ represents a hydrogen atom, or a hydroxy or amino group and $Y_1$ represents a 5-membered heterocyclic group, having 1 to 4 heteroatoms, or a phenyl group, and, when $Y_2$ represents a hydrogen atom, $Y_1$ also represents a cyano or pyridylthio group.

Particularly preferred are the groups of formula VII A, wherein Z represents a butyl or hexyl group which groups may contain a double bond, a phenyl or phenoxy group which groups may be substituted by a hydroxy group, or Z is a 3-amino-3-carboxy-propyl group, and groups of formula VII B, wherein $Y_1$ represents a 2-(3-sydnon), a 2- or 3-thienyl, a phenyl or a 1-tetrazolyl group and when $Y_2$ is a hydrogen atom, $Y_1$ represents a cyano group.

Generally speaking, all penicillanic acid derivatives of formula VI, which can be obtained by fermentative procedures, are particularly suitable starting materials for the preparation of penicillanic sulphoxide derivatives of formula III. These are, for example, the penicillanic acid derivatives of formula VI wherein $R_1$ represents one of the following groups:
phenylacetamido, phenoxy acetamido, 2- or 3-pentenylcarbonamido α-amino-adipoyl-δ-carbonamido, p-hydroxyphenylacetamido n-amylcarbonamido, n-heptylcarbonamido, p-Cl-, p-Br-, and p-I-phenylacetamido, (lower alkyl)mercaptoacetamido, o-F-, m-F- and p-F-phenylacetamido, 2-ethoxy-1-naphthamido and p-amino-phenylacetamido.

Moreover, $R_1$ preferably represents an acylamido side chain derived from known therapeutically active cephalosporins, for example: 2-(3-sydnon)-acetamido, cyanoacetamido, 4-pyridylthioacetamido, 1-tetrazolylacetamido, phthalimido, α-aminophenylacetamido, α-hydroxyphenylacetamido, 2- or 3-thienylacetamido and α-(1,4-cyclohexadienyl)-α-aminoacetamido.

It will be appreciated that before the oxidation of penicillanic acid derivatives of formula VI to the corresponding sulphoxides of formula III A or B, and also before these sulphoxides are reacted with a silicon-containing compound of formula V, as well as in the other processes of the invention described hereinbelow, any groups in the side chain $R_1$, which could be affected during these reactions, such as for example, free amino or hydroxy groups, should be protected before these reactions are carried out. The protection can be effected by methods well known in the art of penicillin and cephalosporin chemistry, and preferably introduces protective groups which can readily be removed again.

The silicon-containing compounds according to the general formula V, some of which are known, can be prepared for example, as follows A silylating agent including the group $(R_{10})_3$ Si- (wherein $R_{10}$ is as hereinbefore defined) and a corresponding imide of the general formula

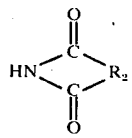

wherein $R_2$ is as hereinbefore defined, is reacted under anhydrous conditions, preferably in an inert organic solvent (for example one of the solvents indicated hereinabove in relation to the process of the invention), or an excess of the silylating agent itself.

The azetidine derivatives of general formula I are versatile intermediates in the preparation of various therapeutically active β-lactam compounds, as will be illustrated by the description of the following processes.

The azetidine derivatives of general formula I can be used to obtain cephalosporanic acid derivatives. It has been established that already during the process of preparing the azetidine derivatives, certain amounts of corresponding Δ³-desacetoxy cephalosporanic acid derivatives are formed in situ, which have been isolated in some instances. Preferably, the azetidine derivatives of formula I are converted into cephalosporanic acid derivatives in a separate reaction step, however.

Thus, according to another feature of the invention, there is provided a new process for the preparation of Δ³-desacetoxycephalosporanic acid derivatives of the general formula:

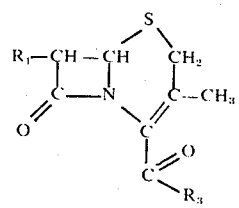   VIII wherein $R_1$ and $R_3$ are as defined in relation to formula I, which comprises cyclising an azetidine derivative of general formula I (wherein the various symbols are as defined in relation to that formula, and moreover, when $R_3$ represents a group $-OR_9$, $R_9$ can also represent a silyl group of the formulae IV A to C, wherein the various symbols are as defined in relation to those formulae) in a dry organic solvent, in the presence of a proton furnishing agent.

By the term "proton furnishing agent" is meant a compound which is able to furnish the catalyzing H⁺ ions which are necessary during the cyclisation reaction. Suitable compounds which may be used for this purpose are hydrogen bromide, hydrogen chloride, toluene-p-sulphonic and concentrated sulphuric acid, hydrogen iodide, perchloric acid, periodic acid, nitric acid, chloric acid, iodic acid, selenic acid, substituted acetic acids such as bromoacetic, trichloroacetic acid and trifluoroacetic acid, substituted sulphonic acids such as trichloromethylsulphonic acid and trifluoromethylsulphonic acid, naphthalenesulphonic acid, oxalic acid, picric acid, and C—H acids, such as tris-(ethylsulphonyl)methane, pentacyanopropene, tetracyanopropene, pentacyanocyclopentadiene, tetracyanocyclopentadiene, tricyanocyclopentadiene and dinitroacetonitrile, or an acid addition salt complex derived from these acids by combination with a nitrogencontaining base, or phosphonium salts derived from these acids by addition to ylide compounds. Suitable bases are aliphatic, cycloalipathic, aromatic or heterocyclic amines, e.g. hexamethylenetetramine, aniline, diphenylamine, N-methylaniline, dimethylaniline, pyridine and quinoline, and pyridine or quinoline substituted by, for example, one or more lower alkyl, aryl(lower)alkyl, aryl or mono- or di(lower)alkylamino groups, such as the picolines, 2-ethylpyridine, 2-propylpyridine, 2,3-dimethylpyridine, 2,5-dimethylpyridine, 2,6-dimethylpyridine, collidines and 2-dimethylaminopyridine, quinoline, isoquinoline, 3-methylisoquinoline, and also pyrazole, imidazole or N-methylimidazole. Preferred bases are pyridine, substituted pyridines, quinoline, substituted quinolines, imidazole and substituted imidazoles. A preferred acid is hydrogen bromide or hydrogen chloride. In principle all bases, with the exception of bases containing a hydroxy group, are suitable to combine with the said acid, but preferably nitrogen-containing bases soluble in the organic solvent employed and having a pKa between 4 and 10 are employed.

The cyclisation of the azetidine derivatives of general formula I into the $\Delta^3$-desacetoxycephalosporanic acid derivatives of formula VIII is preferably carried out at temperatures between 40° and 120°C.

The inert organic solvent employed may be any one of those hereinbefore mentioned in relation to the reaction of compounds of formulae III A or B with the silicon-containing compounds of formula V. Other suitable solvents are for example, chlorobenzene, N,N-dimethylacetamide, dioxan, tetrahydrofuran, triethyleneglycol diethyl ether, butyl acetate, isoamyl acetate, diethyl oxalate, anisole, carbon tetrachloride, dimethylsulphoxide, methyl ethyl ketone and halogenoalkanes, such as 1,2-dichloroethane, 1,1-dichloroethane, 1-bromo-1-chloroethane, 1,2,3-trichloropropane, methylene chloride and chloroform.

The $\Delta^3$-desacetoxycephalosporanic acid derivatives obtained as products of formula VIII can be separated from the reaction mixture by the application of known procedures. When $R_3$ is an amino, hydrazino or ester group, such a group can be converted, if so desired, into a carboxy group by methods know per se.

The $\Delta^3$-desacetoxycephalosporanic acid derivatives of formula VIII have antibiotic properties which make them potentially usual as medicines for human beings and animals, alone or in admixture with other known medically active ingredients. They are preferably employed for therapeutic purposes in the form of the free acid or a non-toxic salt, such as the sodium, potassium or calcium salt.

According to another feature of the invention an azetidine derivative of the general formula:

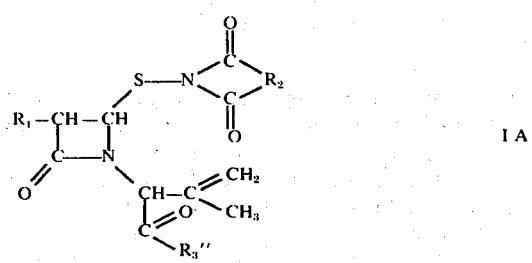

I A wherein $R_1$ and $R_2$ are as hereinbefore defined and $R_3''$ represents an amino, hydrazino or ester group as defined in relation to formula I, may be converted into a 2β-acetoxymethyl-2α-methyl-penam derivative of the general formula:

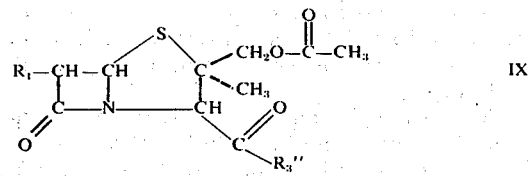

IX wherein $R_1$ and $R_3''$ are as hereinbefore defined. The reaction may be carried out by heating an azetidine derivative of formula I A with thallium (III) acetate, palladium (II) acetate, mercury (II) acetate or manganese (III) acetate in an inert organic solvent, for example, 1,1,2-trichloroethane, t-butanol or benzene, at a temperature between 40° and 120°C.

During this reaction there is usually also obtained a $\Delta^3$-desacetoxycephalosporanic acid derivative of formula VIII, wherein $R_1$ is as hereinbefore defined and $R_3$ has the same significance as indicated for $R_3''$ hereinabove, as well as a 3-acetoxy-cephalosporanic acid derivative of the general formula:

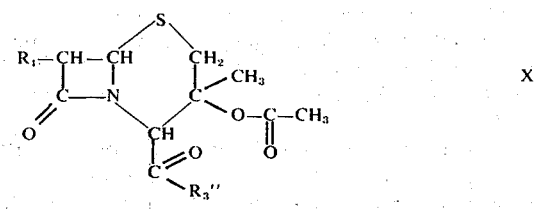

X wherein $R_1$ and $R_3''$ are as hereinbefore defined.

The 2β-acetoxymethyl-penam derivatives of formula IX, some of which are known, proved to be active against gram positive bacteria. These derivatives may also be converted into therapeutically valuable cephalosporins.

A 2β-acetoxymethyl-penam derivative of formula IX may first be oxidized to a corresponding sulphoxide, which may then be converted by a ring expansion process to a cephalosporanic derivative of the general formula:

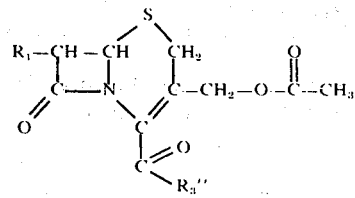

XI wherein $R_1$ and $R_3''$ are as hereinbefore defined. Various cephalosporin derivatives of formula XI are known to have therapeutically interesting properties.

Accordingly, the azetidine derivatives of general formula I, prepared by the process of this invention, may be employed:

a. in a new process of preparing $\Delta^3$-desacetoxycephalosporanic acid derivatives of formula VIII, which have antibiotic properties,
b. to prepare therapeutically active 2β-acetoxymethyl-penam derivatives of formula IX, and
c. as intermediates in a process of preparing therapeutically valuable cephalosporin derivatives of formula XI.

It will be appreciated that the compounds of formulae VIII to XI may also be converted into various other useful derivatives known in the field of penicillins and cephalosporins.

The following Examples illustrate the preparation of compounds of general formula I and the various processes of this invention. Unless indicated otherwise, the PMR spectra were recorded on a Varian A 60 instrument for solutions in deuteriochloroform containing tetramethylsilane as internal reference; the δ-values are given in ppm.

EXAMPLE 1

A. To 400 g (4 moles) of succinimide and 900 ml of triethylamine in 2700 ml of toluene 780 ml of trimethylchlorosilane were added in two hours with vigorous stirring. After refluxing and stirring for an additional hour the mixture was allowed to cool to room temperature. The precipitate was filtered off, washed with 1 l of toluene and 1 l of light petrol (40°–60 °C) and the combined filtrate and washings concentrated to about 700 ml. N-trimethylsilylsuccinimide was isolated by distillation at diminished pressure. The yield was 573 g (3.35 moles) or 83.5%; boiling point 62 °C/0.3 mm Hg. PMR ($CCl_4$) δ:0.38 (s, 9); 2.62 (s, 4).
IR ($CCl_4$): 1770, about 1705, 1326, 1253, about 847 $cm^{-1}$.

B. A mixture of 5.3 g of benzylpenicillin-S-sulphoxide, 50 g of N-acetylsuccinimide, 12.5 ml of N-trimethylsilylsuccinimide and 35 ml of benzene was refluxed for 16 hours. The reaction mixture (containing 1-(1-trimethylsilyloxycarbonyl-2-methylprop-2-enyl)-3-phenylacetamido-4-succinimidothio-azetidin-2-one) was then allowed to cool to room temperature, diluted with benzene (200 ml), treated with decolourizing charcoal, and evaporated to dryness. The residue was purified by column chromatography on silica gel using 5% acetic acid in ethyl acetate as eluent. The fractions containing the major component of the original residue were combined, evaporated to dryness and the residue triturated with diethyl ether. The precipitate was chromatographed a second time to obtain 1-(1-carboxy-2-methylprop-2-enyl)-3-phenylacetamido-4-succinimidothioazetidin-2-one in a pure state. The structure was confirmed by PMR and IR spectroscopy.

PMR δ:1.85 (s, 3); 2.7 (broadened s, 4); 3.65 (s, 2); 4.71 (s, 1); about 5.1 (super imposed signals, 3); about 5.3 (q, J=5 Hz, J'=8 Hz, 1); 7.25 (5); 7.75 (d, J'=8 Hz, about 0.8);
IR (KBr): 3330, 3090, 3062, 3030, 1770, 1718, 1680–1650, 1525, 1495 $cm^{-1}$.

C. A mixture of 25 g (71 mmoles) of benzylpenicillin-S-sulphoxide, 250 ml of dimethylacetamide and 75 ml (78.9 g, 460 mmoles) of N-trimethylsilylsuccinimide was stirred for 4 hours at 105°C. After evaporation in vacuo the residue was dissolved in 250 ml of ethyl acetate and rapidly washed twice with 125 ml of an acetic acid buffer of pH 1.8.

The solution was dried over magnesium sulphate, treated with charcoal and after the addition of 500 ml of toluene concentrated to a small volume. Trituration with diethyl ether and n-hexane yielded 15 g of -(1-carboxy-2-methylprop-2-enyl)-3-phenylacetamido-4-succinimidothio-azetidin-2-one with a purity of 70% as estimated by PMR, using 2,6-dichloroacetophenone as internal standard. Thus the yield of pure azetidinone was 10.5 g (24.3 mmoles) or 34%.

D. 1-(1-carboxy-2-methylprop-2-enyl)-3-phenylacetamido-4-succinimidothio-azetidin-2-one, prepared as described in Example I B, was treated with a diazomethane solution in diethyl ether. After evaporation of the reaction mixture to dryness, the residue was purified by column chromatography on silica gel using a 5:3 (v/v) mixture of toluene and ethyl acetate, and finally only ethyl acetate, as an eluent.

The structure of 1-(1-methoxycarbonyl-2-methylprop-2-enyl)-3-phenylacetamido-4-succinimidothio-azetidin-2-one so obtained was confirmed by mass-spectrometry and PMR and IR spectroscopy.

PMR δ:1.87 (s, 3); 2.81 (s, 4); 3.69 (s); 3.76 (s) together 5; 4.67 (slightly broadened s, 1); 5.08 (centre of $AB_q$, $\delta\nu=0.09$, $J_{AB}=1$ Hz) about 5.15 (d, J=4.4 Hz) together 3; about 5.35 (d, J=4.4 Hz and J'=8.8 Hz, 1); 7.3 and about 7.35 (d) together about 6;
IR (KBr): 3300, 3085, 3065, 3032, 1775, 1720, 1670–1650, 1520 $cm^{-1}$.

EXAMPLE 2

A mixture of 25.5 g (70 mmoles) of the methyl ester of benzylpenicillin-S-sulphoxide, 410 ml of dimethylacetamide, 56 ml (340 mmoles) of N-trimethylsilylsuccinimide and 1.8 ml of acetic acid was stirred for 3.5 hours at 105 °C. After cooling to room temperature the reaction mixture was poured into a cold mixture of 500 ml ethyl acetate and 1500 ml of water. The organic layer was separated and the aqueous layer extracted twice with 250 ml portions of ethyl acetate.

The combined extracts were washed with water, dried over magnesium sulphate and treated with charcoal. The solution was evaporated to dryness and triturated with carbontetrachloride. The residue was filtered off, washed with diethyl ether and dried. There was obtained 1-(1-methoxycarbonyl-2-methylprop-2-enyl)-3-phenylacetamido-4-succinimidothio-azetidin-2-one.

Yield: 19 g (42.7 mmoles) or 61%.

EXAMPLE 3

A mixture of 2.25 g (5 mmoles) of 1-(1-methoxycarbonyl-2-methylprop-2-enyl)-3-phenylacetamido-4-succinimidothio-azetidin-2-one (prepared as described in Example 2) and 1.4 ml (10 mmoles) of triethylamine in 100 ml of tetrahydrofuran was stirred at 65 °C for 25 minutes. The reaction mixture was evaporated, treated with 25 ml of ethyl acetate and evaporated once more. The residual foam was dissolved in 50 ml of ethyl acetate, treated with charcoal and concentrated to a small volume. The desired product crystallized upon cooling. There was obtained 1-(1-methoxycarbonyl-2-methylpropenyl)-3-phenylacetamido-4-succinimidothio-azetidin-2-one.

Yield: 1.25 g (2.9 mmoles) or 58%.

PMR $\delta$:2.11 (s, 3); 2.25 (s, 3); 2.71 (s, 4); 3.69 (s, 2); 3.70 (s, 3); 5.00 (dd, 1; J=8 and =5 Hz); 5.25 (d, 1; J=5 Hz); 6.76 (d, 1; J=8 Hz); 7.3 (s, 5).

IR (KBr): about 3300, about 3065 and about 3030, about 1775, about 1725, 1665, 1385, 1365 and 1140 $cm^{-1}$.

EXAMPLE 4

A. A mixture of 500 mg (1.5 mmoles) of benzylpenicillin-S-sulphoxide, 1.5 ml of N-trimethylsilylsuccinimide, 500 mg of N-acetylsuccinimide and 5 ml of dimethylformamide was stirred at 105 °C for 3.5 hours. The reaction mixture was evaporated in vacuo and the residue triturated with acetone/toluene and the crude substance isolated by filtration.

Yield: 590 mg of a mixture, mainly consisting of succinimide and 1-(1-carboxy-2-methylprop-2-enyl)-3-phenylacetamido-4-succinimidothio-azetidin-2-one.

B. A mixture of 1 g of benzylpenicillin-S-sulphoxide, 3 ml of N-trimethylsilylsuccinimide and 10 ml of dimethylacetamide was heated with stirring at 105 °C for 3.5 hours. After evaporating under reduced pressure the residue of the reaction mixture was treated with 50 ml of ethyl acetate and the solution washed with tw 50 ml portions of an acetic acid/hydrochloric acid buffer of pH 1.8. The ethyl acetate solution was dried over magnesium sulphate, treated with charcoal and after the addition of 100 ml of toluene concentrated to about 10 ml. The crystals formed were isolated by filtration, washed with toluene and diethyl ether and dried.

The yield of 1-(1-carboxy-2-methylprop-2-enyl)-3-phenylacetamido-4-succinimidothio-azetidin-2-one so obtained was 660 mg.

C. The experiment as described in Example 4 B was repeated, but moreover 1 g of N-acetylsuccinimide was added to the reaction mixture.

The yield of 1-(1-carboxy-2-methylprop-2-enyl)-3-phenylacetamido-4-succinimidothio-azetidin-2-one so obtained was 750 mg.

D. The experiment as described in Example 4 B was repeated except that 10 ml of N, N, N', N'-tetramethylurea were used as solvent instead of dimethylacetamide.

The yield of 1-(1-carboxy-2-methylprop-2-enyl)-3-phenylacetamido-4-succinimidothio-azetidin-2-one so obtained was 590 mg.

E. The experiment as described in Example 4 D was repeated, but moreover 1 g of N-acetylsuccinimide was added to the reaction mixture. The yield of 1-(1-carboxy-2-methylprop-2-enyl)-3-phenylacetamido-4-succinimidothio-azetidin-2-one so obtained was 390 mg.

EXAMPLE 5

A. 250 g (1.7 moles) of phthalimide were suspended in 2.75 l of acetonitrile; 250 ml (1.8 moles) of triethylamine were added and the mixture was heated to gentle reflux; 250 ml (1.97 moles) of trimethylchlorosilane were added in 10 minutes and the reaction mixture was then concentrated to a thick paste. 2.5 l of light petrol (80°–110 °C) were added, the triethylammonium hydrochloride was filtered off and washed with 500 ml of light petrol. The filtrate and washings were combined and concentrated until crystallization. After cooling in the refrigerator for several hours N-trimethylsilylphthalimide was isolated by filtration, washed with a small portion of light petrol (40°–60 °C) and dried in vacuo.

Yield: 299 g (1.36 moles) or 80%.

PMR:0.51 (s, 9); 7.73 (centre of super imposed signals, 4).

B. A mixture of 35 g (0.10 mole) of benzylpenicillin-S-sulphoxide, 125 g (0.57 mole) of N-trimethylsilylphthalimide, 260 ml of pure dimethylacetamide and 15 ml (0.1 mole) of trimethylsilyl acetate was heated with stirring for 3.5 hours at 105 °C. The reaction mixture (containing 1-(1-trimethylsilyloxycarbonyl)-2-methylprop-2-enyl)-3-phenylacetamido-4-phthalimidothio-oazetidin-2-one) was cooled to room temperature and concentrated in vacuo (40 °C, 1 mm Hg). The residue was treated with 100 ml of toluene and evaporated to dryness. To the residue a mixture of 250 ml of ethyl acetate, 200 ml of water and 50 g of crushed ice was added.

The pH was adjusted to 1.8 by addition of 4 N-hydrochloric acid and after stirring vigorously for 15 ;1 minutes at 0 °C, the mixture was filtered to remove phthalimide. The organic layer was separated, washed with cold 0.02 N hydrochloric acid and treated with charcoal. The solution was dried with magnesium sulphate, evaporated to dryness and triturated with ethyl acetate. The desired product precipitated and was removed by filtration and washed with a small volume of ethyl acetate. There was obtained 1-(1-carboxy-2-methylprop-2-enyl)-3-phenylacetamido-4-phthalimidothio-azetidin-2-one.

Yield: 46 g with a purity of 70% according to PMR using 2,6-dichloroacetophenone as internal standard. Thus the yield of pure azetidinone was 32 g (67 mmoles) or 67%.

PMR $\delta$:1.89 (s, 3); 3.72 (s, 2); 4.87 (s, 1); 5.08 (broad s, 2); 5.10 (d, 1; J=4.5 Hz; 5.30 (dd, 1, J=4.5 Hz and 8.5 Hz); about 7.25 (super imposed signals, 7); 7.46 (d, 1; J=8.5 Hz); 7.74 (broad s, 2).

IR (KBr): 3300, 3085, 3060, 3030, 1770, 1740, 1712, 1665, 1600, 1530 $cm^{-1}$.

C. To a suspension of 14 g (29 mmoles) of 1-(1-carboxy-2-methylprop-2-enyl)-3-phenylacetamido-4-phthalimidothio-azetidin-2-one (prepared as described in Example 5 B) in 100 ml of tetrahydrofuran a solution of 35 mmoles of diazomethane in diethyl ether was added. The clear solution was treated with acetic acid to remove excess diazomethane and evaporated to dryness. After addition of 100 ml of benzene the solution was filtered, concentrated and chromatographed on a column containing 500 g of silica gel using a 4:1 (v/v) mixture of toluene and ethyl acetate as an eluent. There was obtained 1-(1-methoxycarbonyl-2-methylprop-2-enyl)-3-phenylacetamido-4-phthalimidothio-azetidin-2-one.
Yield: 6.2 g (12.6 mmoles) or 43%.
The structure was confirmed by mass spectrometry, PMR and IR spectroscopy.
PMR δ:1.91 (s, 3); 3.51 (s, 3); 3.77 (s, 2); 4.77 (s, 1); 5.05 (broad s, 1); 5.14 (broad s, 1); 5.13 (d, 1; J=4.5 Hz); 5.40 (dd, 1, J=4.5 Hz and J=8.5 Hz); 7.30 and 7.83 (broad singulets, 4); 7.34 (s, 5) and 7.38 (d, 1; J=8.5 Hz).
IR (KBr): about 3310, 3090, 3067, 3038, about 1780, 1740, 1718, about 1665, 1610, about 1530, 1055 cm$^{-1}$.

EXAMPLE 6

A. A mixture of 3.5 g (10 mmoles) of benzylpenicillin-S-sulphoxide, 13 g (60 mmoles) of N-trimethylsilylphthalimide, 5 g (25 mmoles) of N-acetylphthalimide and 50 ml of dimethylformamide was stirred for 4 hours at 100 °C. After evaporating the reaction mixture in vacuo, the residue was extracted with chloroform and the resulting chloroform solution concentrated and chromatographed on a column. The fractions, which contained the desired final product, were collected and evaporated to dryness. After trituration with n-heptane, the residue was filtered and dried. The yield of 1-(1-carboxy-2-methylprop-2-enyl)-3-phenylacetamido-4-phthalimidothio-azetidin-2-one so obtained was 1.7 g (3.5 mmoles) or 35%. The structure was confirmed by IR and PMR spectroscopy.

B. A mixture of 2.1 g (6 mmoles) of benzylpenicillin-S-sulphoxide, 26 g of N-acetylphthalimide, 7.9 g of N-trimethylsilylphthalimide and 30 ml of toluene was stirred for 3.5 hours at 105 °C. After cooling the mixture was filtered, the filtrate concentrated and chromatographed on a column with silica gel which was acidified with 1% of acetic acid. The column was first eluted with a 4:1 (v/v) toluene-acetone mixture to remove phthalimide and then with a 3:1 (v/v) toluene-acetone mixture containing 0.5% of acetic acid. The fractions containing the desired final product were collected and evaporated to dryness. There was obtained 1-(1-carboxy-2-methylprop-2-enyl)-3-phenylacetamido-4-phthalimidothio-azetidin-2-one.
Yield: 400 mg.

EXAMPLE 7

To a suspension of 14 g (29 mmoles) of 1-(1-carboxy-2-methylprop-2-enyl)-3-phenylacetamido-4-phthalimidothioazetidin-2-one (prepared as described in Example 5 B) in 100 ml of tetrahydrofuran, a solution of 35 mmoles of diazomethane in diethyl ether was added in 1 minute. The excess diazomethane was removed by adding acetic acid to the clear solution, after which the reaction mixture was evaporated to dryness. The residue was dissolved in a mixture of 100 ml of tetrahydrofuran and 7 ml of triethylamine and the solution heated at 67 °C for 15 minutes. The reaction mixture was concentrated in vacuo, the residue dissolved in ethyl acetate, treated with charcoal and again concentrated to a small volume. The concentrate was taken up in carbontetrachloride (about 50 ml), filtered and the filtrate evaporated to dryness. The residue was chromatographed on a column containing 500 g of silica gel, using a 3:1 (v/v) mixture of toluene and ethyl acetate as an eluent. The first product isolated from the column was 7-phenylacetamido-Δdesacetoxycephalosporanic acid (66 mg). The second product which could be isolated was: 1-(1-methoxycarbonyl-2-methylpropenyl)-3-phenylacetamido-4-phthalimidothio-azetidin-2-one.
Yield 6.4 g (13 mmoles) or 45%.
PMR (CDCl$_3$, 60 Mc, δ-values in ppm, TMS as internal reference): δ:2.18 (s, 3); 2.29 (s, 3); 3.59 (s, 3); 3.73 (s, 2); 4.99 (dd, 1; J=5.0 and 7.5 Hz); 5.29 (d,1; J=5.0 Hz); 7.01 (d, 1; J=7.5 Hz), 7.26 (broad s, 2); 7.32 (s, 5); 7.76 (broad s, 2).
IR (KBr): about 3330, 3090, 3068, 3035, 1778, 1742, 1715, 1670, about 1530, 1498, 1052 cm$^{-1}$.

A third fraction obtained from the column contained 4.4'-dithiobis [1-(1-methoxycarbonyl-2-methylpropenyl)-3-phenylacetamidoazetidin-2-one].
Yield: 365 mg (5.2 mmoles) or 18%.
PMR δ:1.98 (s, 3); 2.23 (s, 3); 3.62 (s, 2); 3.76 (s, 3); 4.74 (dd, 1; J=4.5 Hz and 7.5 Hz); 4.97 (d, 1; J=4.5 Hz); 6.81 (d, 1; J=7.5 Hz); 7.31 (s, 5).
IR (KBr): about 3315, 3090, 3065, 3035, 1775, 1728, 1675, about 1525, 1498, 1225, 1075 cm$^{-1}$.

EXAMPLE 8

A. A mixture of 30.2 g (198 mmoles) of hexahydrophthalimide, 60 ml (246 mmoles) of N,O-bis(trimethylsilyl)acetamide and 240 ml of dry acetonitrile was stirred for 16 hours at room temperature and then evaporated to dryness. The residue was crystallized from dry n-heptane; yield: 20.7 g (92 mmoles) of N-trimethylsilylhexahydrophthalimide (46%).
The structure was confirmed by PMR and IR spectroscopy.
PMR δ:0.40 (s, 9); 1.30–1.90 (m, 8); 2.80 (t, 2; J=4 Hz).

B. A mixture of 2.3 g (6.6 mmoles) of benzylpenicillin-S-sulphoxide, 9 g (40 mmoles) of N-trimethylsilyl-hexahydrophthalimide and 30 ml of dimethylformamide was heated during 2 hours at 100 °C. After evaporating the reaction mixture to dryness the residue (which gave virtually one spot on TLC) was purified by column chromatography on silica gel treated with 1% acetic acid, using 3% acetic acid in acetone as an eluent. The fractions containing the major component of the original residue were combined and evaporated to dryness. The residue was chromatographed a second time on silica gel treated with 1% acetic acid, using a 8:2:1 (v/v/v) mixture of toluene, acetone and acetic acid as an eluent. There was obtained 1-(1-carboxy-2-methylprop-2-enyl)-3-phenylacetamido-4-hexahydrophthalimidothio-azetidin-2-one; yield:480 mg.
PMR δ:1.25-2.00 (m, 8); 1.91 (s, 3); 2.95 (s, 2); 3.72 (s, 2); 4.82 (s, 1); 5.09 (s, 2); about 5.16 (d, 1; J=5 Hz); 5.38 (q, 4; J=3 Hz and J=7 Hs); about 7.20 (d, 1); 7.50 (s, 5); 9.25 (s, 1).
IR (CHCl$_3$): 3380, 2940, 1775, 1720, 1665, 1340, 1160 cm$^{-1}$.

EXAMPLE 9

A. A mixture of 28.4 g (20 mmoles) of 1,5,5-trimethylhydantoin, 48 ml (14 mmoles) of N,O-bis(trimethylsilyl)-acetamide and 240 ml of acetonitrile was stirred for 27 hours at room temperature. After evaporating the reaction mixture to dryness, the residue was triturated with n-heptane yielding 19.1 g (8.9 mmoles) of 3-trimethylsilyl-1,5,5-trimethylhydantoin (31%).
PMR δ:0.42 (s, 9); 1.34 (s, 6); 2.84 (s, 2);
IR (CHCl$_3$): 2950, 1755, 1690, 1595 cm$^{-1}$.

B. A mixture of 5.3 g (15 mmoles) of benzylpenicillin-S-sulphoxide, 18 g (90 mmoles) of 3-trimethylsilyl- 1,5,5-trimethylhydantoin, 5.5 g (30 mmoles) of 3-acetyl-1,5,5-trimethylhydantoin and 75 ml of dimethylformamide was stirred for 3 hours at 100 °C. After evaporating the reaction mixture (containing 1-(1-trimethylsilyloxycarbonyl-2-methylprop-2-enyl)-3-phenylacetamido-4-(1,5,5-trimethylhydantoin-3-yl)thio-azetidin-2-one in vacuo, the residue was dissolved in chlorofrom and was chromatographed twice on a silica gel column. The fractions, which contained the desired final product, were collected and evaporated to dryness. After trituration with n-heptane, the residue was filtered and dried. The yield was 1.3 g (2.8 mmoles) of 1-(1-carboxy-2-methylprop-2-enyl)-3-phenylacetamido-4-(1,5,5-trimethylhydantoin-3-yl)thio-azetidin-2-one.

The structure was confirmed by IR and PMR spectroscopy.

PMR δ:1.36 (s, 6); 1.87 (s, 3); 2.85 (s, 3); 3.69 (s, 2); 4.86 (s, 1); 4.99 (1, d; J=4.5 Hz); 5.09 (s, 2); 5.38 (1, q; J=4.5, J'=8.5 Hz); 7.29 (s, 5); 7.77 (1, d; J=8.5 Hz); 8.28 (s, 1).

C. A mixture of 350 mg (1 mmole) of benzylpenicillin-S-sulphoxide, 3.9 g (23 mmoles) of 3-acetyl-1,5,5-trimethylhydantoin, 1.2 g (6 mmoles) of 3-trimethylsilyl-1,5,5-trimethylhydantoin and 5 ml of toluene was stirred for 2 hours at 100°C. After evaporating the reaction mixture to dryness, the residue was purified in the same way as described in Example 8. There were obtained 240 mg of 1-(1-carboxy-2-methylprop-2-enyl)-3-phenylacetamido-4-(1,5,5-trimethylhydantoin-3-yl) thio-azetidin-2-one; yield 51%.

EXAMPLE 10

A. A mixture of 14.1 g (0.1 mole) of 3,3-dimethylglutarimide, 26 ml (0.1 mole) of N,O-bis(trimethylsilyl)acetamide and 120 ml of acetonitrile was stirred for 16 hours at room temperature. After evaporating the solution in vacuo to dryness, the residue was dissolved in 200 ml of n-heptane and this solution was set aside for 16 hours at 0°C. After the crystalline precipitate was filtered off, the filtrate was concentrated to 50 ml and set aside again for 16 hours at 0°C. A second crop of crystals was collected. In this way a total amount of 15.6 g (0.073 mole) of N-trimethylsilyl-3,3-dimethylglutarimide was obtained; yield: 73%.

The structure was confirmed by PMR and IR spectroscopy.

PMR δ:0.38 (s, 9); 1.07 (s, 6); 2.40 (s, 4).

B. A mixture of 2.3 g(6.5 mmoles) of benzylpenicillin-S-sulphoxide, 8.5 g (40 mmoles) of N-trimethylsilyl-3,3-dimethylglutarimide and 30 ml of dimethylformamide was stirred during 3.5 hours at 100°C. After concentrating the reaction mixture (containing 1-(1-trimethylsilyl/carbonyl-2-methylpropenyl)-3-phenylacetamido-4-(3,3-dimethylglutarimido)thio-azetidin-2-one to dryness the residue was dissolved in a mixture of 50 ml of acetic acid and 50 ml of water containing 2% acetic acid.

After adjusting the pH to 1.8 with N 4 hydrochloric acid the layers were separated and the organic layer was treated with decolourizing carbon and concentrated. After evaporating the solvent in vacuo, the residue was dissolved in a small amount of chloroform and chromatographed on a silica gel column treated with 1% acetic acid.

A 5:2:1 (v/v/v) mixture of toluene, acetone and acetic acid was used as an eluent. The major fraction was evaporated to dryness and the residue was washed with some methyl isobutyl ketone. There were obtained 430 mg of 1-(1-carboxy-2-methylpropenyl)-3-phenylacetamido-4-(3,3-dimethylglutarimido)thioazetidin-2-one.

PMR (CDCl$_3$ + DMSO-d6 + CD$_3$COCD$_3$)
δ:1.02 (s, 6); 2.14 (s, 3); 2.27 (s, 3); 2.57 (s, 4); 3.67 (s, 2); 5.05 and 5.15 (dd, 1; J=5 Hz and J=7.5 Hz); 5.37 (d, 1; J=5 Hz); 7.33 (s, 5); 7.94 (d, 1; J=7.5 Hz); 8.93 (s, 1).

IR (KBr): 3320, 2960, 1775, 1700, 1500, 1220, 1120 cm$^{-1}$.

EXAMPLE 11

A. A mixture of 15.5 g (0.1 mole) of 3-ethyl-3-methylglutarimide, 25 ml (0.1 mole) of N,O-bis(trimethylsilyl)acetamide and 120 ml of acetonitrile was stirred for 16 hours at room temperature and concentrated. After dissolving the residue in 50 ml of heptane this solution was set aside at 0°C for 24 hours. The crystalline material was then filtered off, as well as a second crop obtained from the mother liquor.

Yield:3.5 g of N-trimethylsilyl-3-ethyl-3-methylglutarimide.

PMR δ:0.39 (s, 9); about 1.00 (m, 8); 2.39 (s, 4).

B. After adding 9.1 g (40 mmoles) of N-trimethylsilyl-3-ethyl-3-methylglutarimide to a solution of 2.3 g (6.5 mmoles) of benzylpenicillin-S-sulphoxide in 30 ml of dimethylformamide the reaction mixture was stirred during 3.5 hours at 100°C and then concentrated in vacuo. After dissolving the residue (containing 1-(1-trimethylsilyloxycarbonyl-2-methylpropenyl)-3-phenylacetamido-4-(3-ethyl-3-methylglutarimido)thioazetidin-2-one) in a mixture of 50 ml of acetic acid and 50 ml of water containing 2% acetic acid, the pH was adjusted to 1.8 with 4 N hydrochloric acid and the layers were separated. The ethyl acetate layer was treated with decolourizing carbon and concentrated in vacuo; the residue was dissolved in a small amount of chloroform and chromatographed on a silica gel column impregnated with 1% acetic acid, using a 8:2:1 (v/v/v) mixture of toluene acetone and acetic acid as an eluent. The major fraction was evaporated to dryness; there were obtained 120 mg of 1-(1-carboxy-2-methylpropenyl)-3-phenylacetamido-4-(3-ethyl-3-methylglutarimido)thio-azetidin-2-one.

PMR (CDCl$_3$ and a trace of DMSO-d6)
δ:0.86, 0.95 and 0.96 (main signals, 8); 2.15 (s, 4); 2.29 (s, 3); 2.29 (s, 3); 2.55 (s, 4); 3.68 (s, 2); 5.07 and 5.16 (dd, 1; J=5 Hz and J=7.5 Hz); 5.37 (d, 1; J=5 Hz); 7.33 (s, 5); 7.54 (s, 5); about 9.00 (s, broad 1).

IR (KBr): 3350, 2975, 1780, 1700, 1550, 1220 cm$^{-1}$.

EXAMPLE 12

A. To a solution of 20 g (57 mmoles) of phenoxymethylpenicillin-S-sulphoxide in 200 ml of dimethylacetamide was added 60 ml (350 mmoles) of trimethylsilylsuccinimide After stirring the reaction mixture for 3 hours at 100°C, the solvent was removed under reduced pressure and the residue (containing 1-(1-trimethylsilyloxycarbonyl-2-methylprop-2-enyl)3-phenoxyacetamido-4-succinimidothio-azetidin-2-one) was dissolved in a mixture of 200 ml of ethyl acetate and 200 ml of water containing 2% of acetic acid. After adjusting the pH to 1.7 the ethyl acetate layer was treated with decolourizing carbon, diluted with 500 ml of toluene and concentrated. The thus obtained amorphous solid was filtered off, washed with diethyl ether, dissolved in a minimum volume of chloroform and chromatographed on a silica gel column impregnated with 1% acetic acid, using a 6:2:1 (v/v/v) mixture of toluene, acetone and acetic acid as an eluent. The fractions containing the desired product were combined and evaporated in vacuo. There were obtained 2.6 g of 1-(1-carboxy-2-methylprop-2-enyl)-3-phenoxyacetamido-4-succinimidothio-azetidin-2-one.

PMR δ:1.91 (s, 3); 2.79 (s, 4); 4.64 (s, 2); 4.83 (s, 1); 5.16 (s, 2); 5.17 (d, 1; J=4.5 Hz); 5.45 and 5.58 (dd, 1; J=4.5 Hz and J=8 Hz); 6.80-7.40 (m, 5); 8.61 (d, 1; J=8 Hz).

IR (KBr): 3300, 2950, 1775, 1725, 1250, 1150 cm$^{-1}$.

B. A mixture of 550 mg (1.5 mmole) of phenoxymethylpenicillin-R-sulphoxide, 1.5 ml (8.8 mmoles) of N-trimethylsilylsuccinimide and 5 ml of dimethylacetamide was stirred for 2 hours at 80°C and then concentrated.

The oil thus obtained was chromatographed on a silica gel column impregnated with 1% acetic acid, using a 6:2:1 (v/v/v) mixture of toluene, acetone and acetic acid as an eluent. The fractions containing the desired product were combined and evaporated in vacuo. There were obtained 120 mg of white 1-(1-carboxy-2-methylprop-2-enyl)-3-phenoxyacetamido-4-succinimidothio-azetidin-2-one.

The structure was confirmed by PMR and IR spectroscopy.

EXAMPLE 13

A mixture of 12.9 g (30 mmoles) of β-ethoxy-α-naphthyl-penicillin-S-sulphoxide, 30 ml (175 mmoles) of N-trimethylsilylsuccinimide and 100 ml of dimethylacetamide was stirred during 4.5 hours at 100°C. After removing the solvent under reduced pressure and adding 100 ml of toluene to the oily residue, succinimide crystallized. After filtration, the filtrate (containing 1-(1-trimethylsilyloxycarbonyl-2-methylprop-2-enyl)-3-β-ethoxy-α-naphthoylamino-4-succinimidothio-azetidin2-one) was evaporated in vacuo. The residue was dissolved in 150 ml of ethyl acetate and this solution was cooled to 4°C and washed three times with 500 ml of an aqueous acetic acid solution buffered with 4 N hydrochloric acid to pH 2.6.

After drying and treating the ethyl acetate solution with decolourizing carbon, the solvent was removed in vacuo and the residue was purified by chromatography on a silica gel column, using a 1:2:8 (v/v/v) mixture of acetic acid, acetone and toluene as an eluent. There was obtained 1.0 g of 1-(1-carboxy-2-methylprop-2-enyl)-3-β-ethoxy-α-naphthoylamino-4-succinimidothio-azetidin-2-one.

PMR δ:1.31 (t, 3; J=6.5 Hz); 1.80 (s, 1); 2.57 (s, 4); 4.05 (q, 2; J=6.5 Hz); 4.84 (s, 1) 5.00 (s, 2); 5.10 (d, 1; J=4.5 Hz); 5.41 and 5.53 (dd, 1; J=4.5 Hz and J=7.5 Hz); about 6.85–7.80 (m, 6); 8.06 (d, 1: J=7.5 Hz).

IR (KBr): 3300, 3000, 1790, 1780, 1735, 1520, 1310, 1260, 1160 cm$^{-1}$.

EXAMPLE 14

A mixture of 1.8 g (5 mmoles) of phenoxymethylpenicillin-S-sulphoxide and 6.6 g (30 mmoles) of N-trimethylsilylphthalimide in 35 ml of dimethylacetamide was heated at 100°C for 2 hours. The reaction mixture (containing 1-(1-trimethylsilyloxycarbonyl-2-methylprop-2-enyl)-3-phenoxyacetamido-4-phthalimidothioazetidin-2-one) was evaporated to dryness, treated with 30 ml of dichloromethane and filtered. The filtrate was concentrated and purified by chromatography on a silica gel column impregnated with 1% acetic acid, using a 4:1 (v/v) mixture of toluene and acetone with 0.5% acetic acid as an eluent. There was obtained 1-(1-carboxy-2-methylprop-2-enyl)-3-phenoxyacetamido-4-phthalimidothio-azetidin-2-one.

Yield: 1.11 g (2.24 mmoles) or 45%.

PMR δ:1.97 (s, 3); 4.66 (s, 2); 4.85 (s, 1); 5.12 (broad s, 2); 5.24 (d, 1; J=5.0 Hz); 5.50 (dd, 1; J=5.0 Hz and J=8.5 Hz); 6.9–7.9 (super imposed signals, 9); 8.39 (d,1; J=8.5 Hz).

IR (KBr): 3300, 1780, 1740, 1710, 1660, 1590, 1520, 1490, 1360, 1290, 1220, 1170, 1090, 1060 cm$^{-1}$.

EXAMPLE 15

A. A mixture of 200 g (0.57 moles) of benzylpenicillin-S-sulphoxide, 600 ml (3.68 moles) of N-trimethylsilylsuccinimide and 2000 ml of dimethylacetamide was stirred under nitrogen for 5 hours at 100°C. After concentrating, the reaction mixture was diluted with 2000 ml of ethyl acetate and washed three times with a total amount of 1750 ml of a cold buffered solution of 2% acetic acid, adjusted with 2 N hydrochloric acid to pH 1.8.

Then the organic layer was filtered, the filtrate was dried on magnesium sulphate, treated with decolourizing charcoal, concentrated to a thick oil and dissolved in some chloroform. The mixture was chromatographed on a silica gel column using a 1:4 (v/v) mixture of chloroform and toluene, a 5:1 (v/v) mixture of toluene and acetone and a 5:1 (v/v) mixture of toluene and acetone with 1% acetic acid, respectively, as eluents. After repeating this procedure for the right fractions, two products could be isolated, viz. 1-(1-carboxy-2-methylprop-2-enyl)-3-phenylacetamido-4-succinimidothio-azetidin-2-one (19 g) and 7-phenylacetamido-Δ$^3$-desacetoxycephalosporanic acid (10 g). The structures were confirmed by PMR and IR spectroscopy.

B. A solution of 1.1 g (3 mmoles) of 6-phthalimidopenicillanic acid-R-sulphoxide in 20 ml of dimethylacetamide was treated with 4 g (18 mmoles) of N-trimethylsilylphthalimide at 100°C. After 4 hours the mixture (containing 1-(1-trimethylsilyloxycarbonyl-2-methylprop-2-enyl)-3-phthalimido-4-phthalimidothio-azetidin-2-one) was concentrated, the residue was dissolved in 30 ml of dichloromethane and the solution was filtered. The filtrate was purified by chromatography on a silica gel column impregnated with 1% acetic acid, using a 4:1 (v/v) mixture of toluene and acetone containing 0.5% acetic acid as an eluent. There were obtained 100 mg of 7-phthalimido-Δ$^3$-desacetoxycephalosporanic acid and 210 mg of 1-(1-carboxy-2-methylprop-2-enyl)-3-phthalimido-4-phthalimidothio-azetidin-2-one contaminated with dimethylacetamide.

PMR δ2.14 (s, 3); 5.13 (s, 1); 5.32 (s, 2); 5.44 (d, 1, J=5.0 Hz); 5.75 (d, 1, J=5.50 Hz); 7.7–8.1 (super imposed signals, 8).

IR (KBr): 1780, 1770, 1740, 1710, 1600, 1390, 1280, 1050 cm$^{-1}$.

EXAMPLE 16

A mixture of 430 mg of 1-(1-carboxy-2-methylprop-2-enyl)-3-phenylacetamido-4-succinimidothio-azetidin-2-one (prepared as described in Example 1 B), 0.8 ml of N,O-bis(trimethylsilyl) acetamide, 0.2 ml of a 5.8 molar solution of α-picoline hydrobromide in dichloroethane, 0.2 ml of α-picoline and 7 ml of benzene was heated for 3 hours at 80°C. The reaction mixture was then poured into ice-water and ethyl acetate. After washing with ethyl acetate at pH 7, the aqueous layer was extracted with ethyl acetate at pH 3.2. The organic solution was then evaporated to dryness and the residue triturated with diethyl ether. The obtained product was identical to an authentic sample of 7-phenylacetamido-$\Delta^3$-desacetoxy-cephalosporanic acid according to thin-layer chromatography, IR spectroscopy and a microbiological assay using *Escherichia coli* as the test microorganism; yield: 100 mg or 30%.

EXAMPLE 17

A mixture of 45 mg of 1-(1-methoxycarbonyl-2-methylprop-2-enyl)-3-phenylacetamido-4-succinimidothio-azetidin-2-one(prepared as described in Example 1 D),0.05 ml of N,O-bis (trimethylsilyl)acetamide, 0.02 ml of a 5.8 molar solution of α-picoline hydrobromide in dichloroethane, 0.02 ml of α-picoline and 0.7 ml of benzene was heated for 3 hours at 80°C. The reaction mixture was then diluted with 3 ml of ethyl acetate, washed with a hydrochloric acid solution and water, dried on molecular sieves and evaporated to dryness. The residue was then dissolved in chloroform and treated with tetrachloromethane and ligroin. The precipitate was filtered off, washed with ligroin and dried. It was identical to an authentic sample of the methyl ester of 7-phenylacetamido-$\Delta^3$-desacetoxycephalosporanic acid according to thin-layer chromatography; yield: 10 mg or 29%.

The structure was confirmed by IR and PMR spectroscopy.

PMR (CDCl$_3$ and DMSO-d6, 60 Mc) δ:2.09 (s, 3); 3.10 (d, 1; J=18 Hz); 3.47 (d, 1; J=18 Hz); 3.58 (s, 2); 3.78 (s, 3); 4.87 (d, 1; J=4.5 Hz); 5.56 and 5.71 (dd, 1; J=4.5 Hz and J=8 Hz): 7.2 (s, 5); 8.01 (d, 1; J=8 Hz).

IR (KBr): 3275, 1770, 1720, 1640, 1530 cm$^{-1}$.

EXAMPLE 18

A mixture of 3.8 g (8.5 mmoles) of 1-(1-methoxycarbonyl-2-methylprop-2-enyl)-3-phenylacetamido-4-succinimidothio-azetidin-2-one (prepared as described in Example 1 D), 3.4 g (8.3 mmoles) of thallium (III) acetate. 1.5 H$_2$O and 175 ml of 1,1,2-trichloroethane was stirred under nitrogen for 4 hours at 80°C. The solvent was removed in vacuo, the residue was extracted with methylene chloride and ethyl acetate. After concentrating the extract, the residue was dissolved in a small amount of chloroform and separated by chromatography on a silica gel column, using a 1:1 (v/v) mixture of toluene and ethyl actate as an eluent. There were obtained two fractions, described in order of elution.

The first fraction was evaporated to dryness, the residue was dissolved in a small volume of methylene chloride. Upon precipitation with diethyl ether there were obtained 120 mg of the methyl ester of 7-phenylacetamido-$\Delta^3$-desacetoxycephalosporanic acid.

From the mother liquor of this fraction could be obtained 360 mg of another compound: methyl 2β-acetoxymethyl-2α-methyl-6β-phenylacetamidopenam-3α-carboxylate in the form of an oily residue.

PMR δ:1.45 (s, 3); 2.02 (s, 3); 3.63 (s, 2); 3.77 (s, 3); 3.64 and 4.31 (ABq, 2; J=12 Hz); 4.64 (s, 1); 5.53 (d, 1; J=4 Hz); 5.65 (dd, 1; J=4 Hz and J=9 Hz); 6.81 (d, 1; J=9 Hz); 7.29 (s, 5).

IR (CHCl$_3$): 3370, 1780, 1750, 1680, 1500 cm$^{-1}$. The second fraction was concentrated in vacuo and chromatographed a second time. There were obtained 360 mg of methyl 3-acetoxy-3-methyl-7-phenylacetamidocepham-4-carboxylate.

PMR δ1.52 (s, 3); 1.80 (s, 3); 3.24 and 3.69 (ABq, 2; J=14 Hz); 3.64 (s, 2); 3.75 (s, 3); 4.70 (s, 1); 5.24 (d, 1; J=4.5 Hz); 5.47 and 5.61 (dd, 1; J=4.5 Hz and J=9 Hz); 6.28 (d, 1; J=9 Hz); 7.29 (s, 5).

IR (CHCl$_3$): 3430, 1770, 1750, 1680, 1500 cm$^{-1}$.

EXAMPLE 19

A mixture of 4.4 g (10 mmoles) of the benzyl ester of benzylpenicillin-S-sulphoxide, 12.5 g (57 mmoles) of N-trimethylsilylphthalimide, 0.2 ml (4 mmoles) of acetic acid and 26 ml of dimethylacetamide was stirred for 3 hours at 105°C. The dimethylacetamide was evaporated, while toluene was added, whereafter phthalimide was filtered off. To the filtrate were added 50 ml of ethyl acetate and water, adjusted with hydrochloric acid to pH 2. After stirring for 5 minutes a second crop of phthalimide was filtered off, the two layers were separated and the organic layer was washed with water, treated with decolourizing carbon, dried with magnesium sulphate and concentrated to dryness. The residue was extracted with a small amount of toluene (10-25 ml) and this extract was chromatographed on a silica gel column, using toluene-ethylacetate mixtures (from 5:1 to 3:2; v/v) as eluents. There were obtained 300 mg of 1-(1-benzyloxycarbonyl-2-methylprop-2-enyl)-3-phenylacetamido-4-phthalimidothio-azetidin-2-one.

PMR δ:1.92 (s, 3); 3.73 (s, 2); 4.89 (s, 1); 5.08 (s, 3); 5.12 (s, 1); 5.18(d,1; J=4.5 Hz); 5.36 (dd, 1; J=4.5 Hz and J=8 Hz); 7.26 (d, 1; J=8 Hz); about 7.20–7.60 (m, 10); 7.77 (s, 4).

IR (KBr): 3300, 1775, 1735, 1705, 1660, 1280, 1050 cm$^{-1}$.

Another crop of 3.4 g of the same product was obtained which was still contaminated with some starting material.

EXAMPLE 20

A mixture of 4.8 g (10 mmoles) of the p-nitrobenzyl ester of benzylpenicillin-S-sulphoxide, 12.5 g (57 mmoles) of N-trimethylsilylphthalimide, 0.1 ml (2 mmoles) of acetic acid and 26 ml of dimethylacetamide was stirred for 4 hours at 105°C. The solvent was removed under reduced pressure and to the oily residue were added 50 ml of ethyl acetate and 100 ml of water; the mixture was acidified with hydrochloric acid to pH 2. The mixture, which contained a precipitate, was treated with decolourizing carbon and filtered. The organic layer was washed with water, dried and evaporated.

The residue was extracted with a small amount of toluene (25 ml) and this extract was chromatographed through silica gel using a 4:1 (v/v) mixture of toluene and ethyl acetate as an eluent. This afforded a foam, which was treated with decolourizing carbon in ethyl acetate. After filtration and evaporation to dryness, there were obtained 140 mg of 1-(1-p-nitrobenzyloxycarbonyl-2-methylprop-2-enyl)-3-phenylacetamido-4-phthalimidothio-azetidin-2-one.

PMR δ:1.91 (s, 3); 3.76 (s, 2); 4.97 (s, 1); 5.07 (d, 1; J=4.5 Hz); 5.07 (s, 1); 5.15 (s, 1); 5.18 (s, 1); 5.32 (dd, 1; J=4.5 Hz and J=8 Hz); 7.27 (d, 1; J=8 Hz); 7.36 (s, 5); 7.44 (d, 2; J=8.5 Hz); 7.78 (s, 4); 8.11 (d, 2; J=8.5 Hz).

IR (KBr): 3400, 1780, 1740, 1710, 1510, 1350, 1290, 1060 cm$^{-1}$.

The second component eluted was the isomer 1-(1-p-nitrobenzyloxycarbonyl-2-methylpropenyl)-3-phenylacetamido-4-phthalimidothioazetidin-2-one (511 mg), isolated as a crystalline material from ethyl acetate.

PMR δ:2.25 (s, 3); 2.35 (s, 3); 3.75 (s, 2); 4.91 (dd, 1; J=5.5 Hz and J=7.5 Hz); 507 and 5.32 (q, 2; J=14 Hz); 518 (d, 1; J=5.5 Hz); 6.67 (d, 1; J=7.5 Hz); 7.38 (s, 5); 7.42 (d, 2; J=8.5 Hz); 7.83 (s, 4); 8.07 (d, 2; J=8.5 Hz);

IR (KBr): 3350, 1785, 1740, 1720, 1520, 1355, 1300, 1230, 1070, 1080 cm$^{-1}$.

EXAMPLE 21

A mixture of 5 g (10 mmoles) of the trimethylsilylester of benzylpenicillin-S-sulphoxide, 12.5 g (57 mmoles) of N-trimethylsilylphthalimide, 0.6 ml (10 mmoles) of acetic acid and 26 ml of dimethylacetamide was stirred for 3.5 hours at 105°C. The reaction mixture was cooled to room temperature and concentrated in vacuo.

To the residue was added 100 ml of cold ethyl acetate and 50 ml of cold water, acidified with hydrochloric acid (pH 1.5). The mixture was filtered and the organic layer was washed with water, treated with decolourizing carbon, dried and evaporated. The residue was extracted with a small amount of toluene. This extract was treated with decolourizing carbon and the solvent was removed in vacuo.

There were obtained 3.8 g of 1-(1-carboxy-2-methylprop-2-enyl)-3-phenylacetamido-4-phthalimidothio-azetidin-2-one; yield 79%. The structure was confirmed by PMR and IR spectroscopy.

EXAMPLE 22

A mixture of 2.8 g (7 mmoles) of the t-butylamide of benzylpenicillin-S-sulphoxide, 8.8 g (40 mmoles) of N-trimethylsilylphthalimide, 0.2 ml (4 mmoles) of acetic acid and 18 ml of dimethylacetamide was stirred for 3.5 hours at 105°C. After cooling the reaction mixture was poured out into 150 ml of water and 50 ml of ethyl acetate. The layers were separated and the water layer was extracted three times with ethyl acetate. The combined organic layers were dried and concentrated. After filtration of the precipitated phthalimide, n-hexane was added to the filtrate. There were obtained 3.5 g of a solid material, which gave virtually one spot on the thin-layer chromatogram. After chromatography through silica gel, using mixtures of toluene and ethyl acetate (from 4:1 to 2:1; v/v) as eluents, there were obtained: 900 mg of 1-(1-t-butylamidocarbonyl-2-methylprop-2-enyl)-3-phenylacetamido-4-phthalimidothio-azetidin-2-one; yield 24%.

PMR (DMSO-d6; 60 Mc) δ:1.26 (s, 9); 1.80 (s, 3); 3.69 (s, 2); 4.90 (broad s, 3); 4.97 (dd, 1; J=5 Hz and J=7 Hz); 5.35 (d, 1; J=5 Hz); 7.36 (s, 5); 7.96 (s, 4); 9.37 (d, 1; J=7 Hz).

IR (KBr): 3350, 2970, 1780, 1730, 1710, 1650, 1530, 1290, 1060 cm$^{-1}$.

EXAMPLE 23

A mixture of 7 g (20 mmoles) of benzylpenicillin-S-sulphoxide, 21 ml (336 mmoles) of N-trimethylsilylsuccinimide and 70 ml of dimethylacetamide was stirred for 3,5 hours at 105°C. After removing the solvent in vacuo, adding some toluene and removing the toluene in vacuo, the residue was stirred in a mixture of ethyl acetate and water (pH = 1.5) at 0°C. The organic layer was then treated with decolourizing charcoal dried and concentrated. After filtering off the precipitate, the filtrate was diluted with ethyl acetate to a volume of 200 ml. To this solution was added 16 ml of a 0.46 molar solution of potassium-2-ethyl caproate in n-propanol and a few drops of diethyl ether. The precipitate, the potassium salt of 1-(1-carboxy-2-methylprop-2-enyl)-3-phenylacetamido-4-succinimidothio-azetidin-2-one, was filtered off, washed with diethyl ether and dried; yield: 2.24 g.

PMR (DMSO-d$_6$): δ: 1.85 (s, 3); 2.72 (s, 4); 3.62 (s, 2); 4.56 (s, 1); 4.95 (s, broad, 1); 5.14 (dd, 1; J=5 Hz and J=8 Hz); 5.50 (d, 1; J=5 Hz); 7.35 (s, 5); 9.18 (d, 1; J=8 Hz)

IR (KBr): 3350, 1760, 1720, 1660, 1610, 1315, 1160 cm$^{-1}$

We claim:

1. Azetidine derivatives of the formula

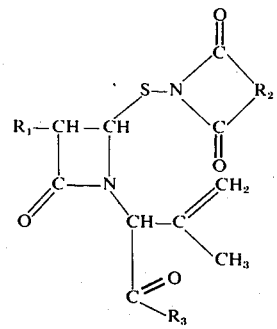

wherein $R_1$ represents a penicillin- or cephalosporin acylamido group, $R_2$ represents:

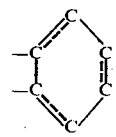

and when said group represents a phenylene - this group may carry one to four further substitutents selected from the group consisting of halogen and lower alkyl, lower alkenyl and phenyl $R_3$ represents an amino group of the formula

wherein $R_7$ represents a hydrogen atom or a lower alkyl and $R_8$ represents a lower alkyl, or $R_3$ represents a N,N'-disubstituted hydrazino group wherein the substituents are lower alkyl, or $R_3$ represents —$OR_9$, wherein $R_9$ represents a hydrogen atom, a lower alkyl optionally substituted by 1 to 3 halogen atoms or by 1 or 2 phenyl groups, wherein the phenyl groups may be substituted by a methoxy or a nitro, or $R_9$ represents a phenacyl group or an alkali metal or alkaline earth metal ion and corresponding azetidine derivatives wherein the double bond in the propenyl side chain has been shifted from the 2- to the 1-position.

2. Azetidine derivatives according to claim 1, wherein the group

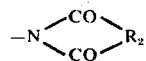

represents a phthalimido and hexahydrophthalimido group.

3. Azetidine derivatives according to claim 1, wherein $R_9$ is selected from the group consisting of alkali metal and alkaline earth metal ions.

4. Azetidine derivatives according to claim 1, wherein $R_9$ represents a hydrogen atom, a methyl or benzyl group or a sodium or potassium ion.

5. Azetidine derivatives according to claim 1, wherein $R_9$ represents a hydrogen atom or methyl group.

6. Azetidine derivatives according to claim 1, wherein the group

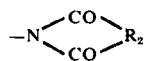

represents a phthalimido group and $R_9$ represents a hydrogen atom or a methyl group.

7. Azetidine derivatives according to claim 1, wherein $R_1$ represents a group of the general formula:

      VII wherein $Q_1$ represents a hydrogen atom or a group linked to the nitrogen atom by a carbon or sulphur atom, and $Q_2$ represents a hydrogen atom or a lower alkyl, hydroxy, amino or phenyl(lower) alkyl group, or $Q_1$ and $Q_2$ together with the nitrogen atom to which they are attached collectively represent a heterocyclic group, or $Q_1$ and $Q_2$ together form an aralkylidene or alkylidene group.

8. Azetidine derivatives according to claim 1, wherein $R_1$ represents a group of the general formula:

wherein $Q_2$ represents a hydrogen atom and $Q_1$ is a group of the following formula:

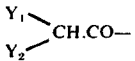      VII B and $Y_2$ represents a hydrogen atom, or a hydroxy or amino group and $Y_1$ represents a 5-membered heterocyclic group, having 1 to 4 heteroatoms, or a phenyl group, and, when $Y_2$ represents a hydrogen atom, $Y_1$ also represents a cyano or pyridylthio group.

9. Azetidine derivatives according to claim 1, wherein $R_1$ represents a group of the general formula:

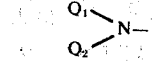

wherein $Q_2$ represents a hydrogen atom and $Q_1$ is a group of the following formula:

Z CH$_2$ CO —      VII A wherein Z represents:
a. an aliphatic hydrocarbon group having at most 6 carbon atoms and which can have a double bond,
b. a phenyl or phenoxy group, which groups may be substituted by halogen atoms, or hydroxy, lower alkyl, lower alkoxy, nitro or amino groups,
c. a(lower alkyl)thio group, or
d. a 3-amino-3-carboxy-propyl group.

10. Azetidine derivatives according to claim 8, wherein $Y_1$ represents a 2-(3-sydnon), a 2- or 3-thienyl, a phenyl or a 1-tetrazolyl group, and when $Y_2$ is a hydrogen atom, $Y_1$ represents a cyano group.

11. Azetidine derivatives according to claim 9, wherein Z represents a 3-amino-3-carboxy-propyl group, a butyl or hexyl group which groups may contain one double bond, or a phenyl or phenoxy group which groups may be substituted by a hydroxy group.

12. Azetidine derivatives according to claim 1, wherein $R_1$ is selected from the group consisting of the following groups:
phenylacetamido, phenoxy acetamido, 2-or 3-pentenylcarbonamido α-amino-adipoyl-δ-carbonamide, p-hydroxyphenylacetamido n-amylcarbonamido, -n-heptylcarbonamido, p-Cl-, p-Br-, and p-I-phenylacetamido, (lower alkyl)mercaptoacetamido, o-F-, m-F-and p-F-phenylacetamido, 2-ethoxy-1-naphthamido, p-aminophenylacetamido, 2-(3-sydnon)-acetamido, cyanoacetamido, 4-pyridylthioacetamido, 1-tetrazolylacetamido, phthalimido, α-aminophenylacetamido, α-hydroxyphenylacetamido, 2- or 3-thienylacetamido and α-(1,4-cyclohexadienyl)-α-aminoacetamido.

13. Azetidine derivatives according to claim 1, wherein $R_1$ represents a phenylacetamido group, the group:

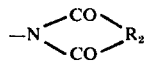

represents a phthalimido group and $R_9$ represents a hydrogen atom or a methyl group.

14. Azetidine derivative according to claim 1, which is 1-(1-carboxy-2-methylprop-2-enyl)-3-phenylacetamido-4-phthalimidothio-azetidin-2-one.

15. Azetidine derivative according to claim 1, which is 1-(1-methoxycarbonyl-2-methylprop-2-enyl)-3-phenylacetamido-4-phthalimidothioazetidin-2-one.

16. Azetidine derivative according to claim 1, which is 1-(1-methoxycarbonyl-2-methylpropenyl)-3-phenylacetamido-azetidin-2-one.

17. Azetidine derivative according to claim 1, which is 1-(1-carboxy-2-methylprop-2-enyl)-3-phenylacetamido-4-hexahydrophthalimidothioazetidin-2-one.

18. Azetidine derivative according to claim 1, which is 1-(1-carboxy-2-methylprop-2-enyl)-3-phenoxyacetamido-4-phthalimidothio-azetidin-2-one.

19. Azetidine derivative according to claim 1, which is 1-(1-carboxy-2-methylprop-2-enyl)-3-phthalimido-4-phthalimidothio-azetidin-2-one.

20. Azetidine derivative according to claim 1, which is 1-(1-benzyloxycarbonyl-2-methylprop-2-enyl)-3-phenylacetamido-4-phthalimidothioazetidin-2-one.

21. Azetidine derivative according to claim 1, which is 1-(1-p-nitrobenzyloxycarbonyl-2-methylprop-2-enyl)-3-phenylacetamido-4-phthalimidothio-azetidin-2-one.

22. Azetidine derivative according to claim 1, which is 1-(1-p-nitrobenzyloxycarbonyl-2-methylpropenyl)-3-phenylacetamido-4-phthalimidothio-azetidin-2-one.

23. Azetidine derivative according to claim 1, which is 1-(1-t-butylamidocarbonyl-2-methylprop-2-enyl)-3-phenylacetamido-4-phthalimidothio-azetidin-2-one.

* * * * *